United States Patent [19]  [11] 4,118,480
Williams  [45] Oct. 3, 1978

[54] PHARMACEUTICAL PREPARATION FOR TREATING HEMORRHOIDS AND ANAL FISSURES

[75] Inventor: Glenn L. Williams, Lafayette Hill, Pa.

[73] Assignee: Charles V. Stoelker, Philadelphia, Pa.

[21] Appl. No.: 496,276

[22] Filed: Aug. 9, 1974

Related U.S. Application Data

[63] Continuation-in-part of Ser. No. 331,081, Feb. 9, 1973, abandoned.

[51] Int. Cl.$^2$ .................... A61K 33/24; A61K 31/47; A61K 31/245; A61K 31/05
[52] U.S. Cl. .................... 424/131; 424/180; 424/258; 424/310; 424/346
[58] Field of Search .............. 424/131, 310, 258, 346, 424/180

[56] References Cited

U.S. PATENT DOCUMENTS

| | | | |
|---|---|---|---|
| 439,581 | 10/1890 | Hall | 424/131 |
| 1,674,353 | 6/1928 | Brockett | 424/346 |
| 1,676,554 | 7/1928 | Hoopman | 424/346 |

OTHER PUBLICATIONS

*Remington's Pharmaceutical Sciences,* Martin et al., Mack Pub. Co., Easton, Penna., 1965, pp. 1420–1421.
*Physicians' Desk Reference,* Medical Economics, Inc., 22nd Ed., (1968) p. 623.
*Handbook of Non-Prescription Drugs* —(1967)— American Pharmaceutical Assoc., pp. 72–76.
*PDR,* pp. 839–840.

*Primary Examiner*—Frederick E. Waddell
*Attorney, Agent, or Firm*—Harding, Early & Follmer

[57] ABSTRACT

A pharmaceutical preparation for treating hemorrhoids and anal fissures comprising 0.6 gr phenol, 0.3 gr menthol, 10 gr bismuth subnitrate, 10 gr pulverized starch, and 50 gr of 1% by weight dibucaine in an ointment base of lanolin and petrolatum.

2 Claims, No Drawings

PHARMACEUTICAL PREPARATION FOR TREATING HEMORRHOIDS AND ANAL FISSURES

CROSS-REFERENCE TO RELATED APPLICATIONS

This patent application is a continuation-in-part of my patent application Ser. No. 331,081, now abandoned filed Feb. 9, 1973.

BACKGROUND OF THE INVENTION

There are presently available pharmaceutical preparations for treating hemorrhoids and anal fissures. One of these is NUPERCAINAL ointment, which is described in the Physicians' Desk Reference To Pharmaceutical Specialities And Biologicals, published by Medical Economics, Inc., a subsidiary of Chapman-Reinhold, Inc., Oradell, New Jersey, Twenty-Second Edition, 1968, page 623, as an ointment containing dibucaine in an ointment base of lanolin and petrolatum. NUPERCAINAL ointment is a product of Madison Laboratories, a division of Ciba Pharmaceutical Company, Summit, New Jersey, and is described as a soothing and long-acting local anesthetic. The high potency of NUPERCAINAL ointment permits therapeutic effectiveness with low concentration. NUPERCAINAL ointment is recommended for relief of pain and itching in hemorrhoids, anal fissures, etc.

However, NUPERCAINAL ointment is a very thin, slippery ointment that melts easily under body heat and disappears into the tissues, and does not provide a coating or cover for the treated tissue.

SUMMARY OF THE INVENTION

It is an object of the present invention to provide a pharmaceutical preparation for the treatment of hemorrhoids, anal fissures, etc. which acts as a long-lasting quick-acting and low sensitizing local anesthetic, which provides a protective coating for the treated tissues, which relaxes spasms to a great extent and improves blood circulation and healing, which has an astringent effect that shrinks the treated tissues to encourage healing, and that has a cooling, soothing effect when applied to the treated tissue.

The object of the invention are accomplished by mixing a number of ingredients in such amounts and proportions by weight so as to accomplish the desired result.

DESCRIPTION OF THE PREFERRED EMBODIMENT

The novel medical preparation of this invention, in its most preferred form, comprises: phenol, menthol, bismuth subnitrate, pulverized starch, and dibucaine in an ointment base.

Phenol, carbolic acid, $C_6H_5OH$, is an antiseptic and also has a local anesthetic effect. The phenol is about 1% by weight of the inventive pharmaceutical preparation because this has been found to be a safe level. If much more phenol is used in the preparation, the phenol may cause macerations of the treated tissues; if much less phenol is used in the preparation, the phenol is not effective.

In mixing the ingredients of the inventive preparation, the phenol may be mixed in 95% liquified form, or in crystal form. Usually, the 95% liquified phenol is used because it is difficult to keep the phenol in its crystal form because it takes up water so easily. The 95% liquified phenol is 95% phenol and 5% water, with the phenol taking up water and stabilizing at that ratio. The term "phenol" as used herein refers to this 95%-5% liquid. All ratios and percentages of ingredients herein are by weight.

The phenol has an anesthetic effect and a stimulating healing effect which are long acting. Its anesthetic effect is greater than the anesthetic effect of the NUPERCAINAL ointment, but is not as fast acting. Additionally, the phenol has some astringent effect to assist in shrinking the hemorrhoids or treated tissue.

Menthol, a colorless, crystalline alcohol, $C_{10}A_{20}O$, is used in the inventive pharmaceutical preparation primarily for its cooling effect. Also, the menthol counteracts or minimizes any tissue-destroying effect of the phenol, which is a potent antiseptic. It is preferably half the amount by weight of the phenol and it neutralizes some of the toxic effects of the phenol. The crystalline menthol is liquified by the phenol so that the preparation is easy to mix.

The ratio of phenol is menthol is important and cannot be varied too much from the preferred ratio of 2 to 1. If the concentration of phenol is increased, it imparts an irritating burning effect to the treated tissues because the quantity of menthol is not sufficient to neutralize this effect of the phenol and give the inventive preparation a soothing effect. On the other hand, if the concentration of methol is increased, it precipitates out of the preparation foaming crystals in the ointment that irritate the treated tissues.

The bismuth subnitrate is an astringent that shrinks the tissues and encourages healing. Other bismuths are available and can be used in the inventive preparation. However bismuth subnitrate is the preferred bismuth because it is very stable and does not have any objectionable staining qualities. For example, bismuth suboxylate could be used but it is so unstable that when you mix it into the other ingredients of the inventive pharmaceutical preparation, it causes the preparation to deteriorate and cause slow leaks of gas.

Another bismuth that could be used in the inventive preparation is bismuth subgallate. However, bismuth subgallate has a brownish color that stains, and that is objectionable so the bismuth subnitrate is preferred because it is perfectly white and does not stain. Bismuth compounds of this type have a very tenacious effect to cause ointment to adhere to slippery tissues to which it is applied.

In addition to providing an astringent effect which shrinks the hemorrhoids, the bismuth subnitrate aids in thickening the inventive preparation so that it provides a protective coating to the treated tissues.

The pulverized starch serves to thicken the inventive pharmaceutical preparation so that is forms a paste that covers and sticks to the treated tissues.

The NUPERCAINAL ointment comprises 1% dibucaine in a lanolin and petrolatum ointment base, with ½% acetone sodium bisulfits as a preservative. Other local anesthetic ointments could be used instead of the NUPERCAINAL ointment, if desired. For example, 20% benzocaine in a lanolin and petrolatum ointment base, by weight, may be used instead of the NUPERCAINAL ointment. The 20% benzocaine ointment is approximately the equivalent in anesthetic strength to the 1% NUPERCAINAL ointment. The 20% benzocaine ointment is a long-acting local anesthetic.

The preferred inventive preparation with the 1% dibucaine ointment is of such low concentration of the active ingredient, dibucaine, that very few patients have a sensitive reaction to its use, although occasionally a patient does become allergic to the preferred preparation and they have to stop using it.

The other preparation using a higher concentration of local anesthetic, such as the 20% benzocaine ointment, give the same effect as the lower concentration of the dibucaine. However, because of the high concentration of benzocaine, many more patients, comparatively, become sensitive to the preparation. If a patient is allergic or sensitive to one of the inventive preparations, the patient stops using that preparation and tries another. If he is sensitive to all of them, which is very unusual, he must stop using all of the inventive preparations.

Patients using the inventive pharmaceutical preparation derive much more benefit from its use than patients using just a local anesthetic, and they get more benefit from the inventive preparation than if they used the ingredients thereof separately. Combining the ingredients into the inventive preparation gives a thick paste that sticks to the treated area and provides a protective cover. The pulverized starch assists in thickening the composition, and so does the bismuth subnitrate, in addition to giving the preparation astringent properties that assist in shrinking the treated tissue and anesthetic action that relieves spasms, thus promoting better blood circulation to aid in healing.

The inventive preparation does not melt and disappear, but remains as a protective coating that relieves the pain of hemorrhoids and also shrinks them. It has an astringent effect that contracts the tissues, diminishing discharges, and promoting healing. On application, it feels cool and soothing rather than hot and burning. This cooling effect is due primarily to the presence of the correct proportion of menthol. If the menthol were omitted from the inventive preparation, on application it would burn like fire. For example, if the mixture of phenol and NUPERCAINAL ointment were placed on a raw, sore tissue, it would feel hot and irritable and unpleasant upon application.

In regard to piles and hemorrhoids, one of the factors that slows healing is poor blood circulation and pain in the sphincter muscles. There are two types of sphincter muscles, the internal and the external. Pain causes the sphincter muscles to go into spasm: a sudden, abnormal, involuntary muscle contraction. If you can relieve the spasm by relieving the pain, blood circulation improves and that immediately encourages healing. This is also true of anal fissures.

An anal fissure is a crack in the mucosa of the anal canal wich usually occurs at the anal crypts. They can be extremely painful. Placing the inventive preparation directly on the anal fissure coats it, anesthetizes it, and provides an agreeable cooling feeling. It relaxes the spasms to a great extent and encourages the body to improve circulation of the blood and healing. The inventive preparation, primarily from the phenol, acts as an antiseptic to any bacteria which would keep the anal fissure open, and many minor anal fissures heal completely in two or three days during treatment with the inventive preparation.

The inventive pharmaceutical preparation is a paste which, in addition to covering and sticking to the treated tissue, is easier to apply than thinner ointments which are difficult even to keep on the fingers.

The inventor, a medical doctor, has used the inventive composition quite frequently in post partum (after child-birth) cases where the patient has very severe hemorrhoids. Many of the patients also have fissures and cracks, which are quite irritated prior to treatment. Treatment by the inventive ointment, one to four times daily as needed, invariably results in the patients telling the inventor that they get prompt relief. Very rarely does the inventor find a patient who develops sensitivity to the inventive preparation.

The following examples are not limiting but are illustrative of pharmaceutical preparations of this invention.

EXAMPLE 1

| Ingredients: | Amounts, gr. |
| --- | --- |
| phenol | 0.6 |
| menthol | 0.3 |
| bismuth subnitrate | 10.0 |
| pulverized starch | 10.0 |
| 1% by weight dibucaine in an ointment base of lanolin and petrolatum (Ciba's NUPERCAINAL ointment) | 50.0 |

The ingredients are mixed to make a smooth paste.

The paste is applied locally well up into the anal canal to cover the treated tissue, one to four times daily, as needed.

EXAMPLE 2

The ingredients and amounts of Example 1 are mixed together except 0.8 gr of phenol and 0.4 gr of menthol are used.

EXAMPLE 3

The ingredients and amounts of Example 1 are mixed together except 0.7 gr of phenol and 0.35 gr of menthol are used.

EXAMPLE 4

The ingredients and amounts of Example 1 are mixed together except 0.5 gr of phenol and 0.25 gr of menthol are used.

EXAMPLE 5

The ingredients and amounts of Example 1 are mixed together except 1.4 gr of phenol and 0.7 gr of menthol are used.

EXAMPLE 6

The ingredients and amounts of Example 1 are mixed together except 0.36 gr of phenol and 0.18 gr of menthol are used.

EXAMPLE 7

The ingredients and amounts of Example 1 are mixed together except the 50 gr dibucaine ointment is replaced by an equivalent anesthetic strength benzocaine ointment, 50 gr 20% benzocaine in an ointment base of lanolin and petrolatum.

To summarize Examples 1 to 7, the pharmaceutical preparation for treating hemorrhoids and anal fissures comprises as ingredients in the proportions by weight of about 1.4 to 0.36 parts phenol, 0.7 to 0.18 parts menthol, 10 parts bismuth subnitrate, 10 parts pulverized starch, and 50 parts of 1% dibucaine or 20% benzocaine in an ointment base, the ratio of phenol to menthol being about 2 to 1.

What I claim is:

1. A pharmaceutical preparation of treating hemorrhoids and anal fissures, comprising as ingredients in the proportions by weight of about 1.4 to 0.36 parts phenol, 0.7 to 0.18 parts menthol, 10 parts bismuth subnitrate, 10 parts pulverized starch, and 50 parts of 1% dibucaine or 20% benzocaine in an ointment base, the ratio of phenol to menthol being about 2 to 1, said menthol being sufficient in amount to neutralize the unwanted astringent properties of the phenol and less than the amount to cause crystallization of the menthol, the ingredients include and are in the proportions by weight of 0.6 gr phenol, 0.3 gr menthol, 10 gr bismuth subnitrate, 10 gr pulverized starch, and 50 gr of 1% by weight of dibucaine in an ointment base of lanolin and petrolatum.

2. A method of treating hemorrhoids and anal fissures comprising externally applying to the surface of the tissue to be treated a pain-killing coating of a pharmaceutical preparation comprising as ingredients in parts by weight about 1.4 to 0.36 parts phenol, 0.7 to 0.18 parts menthol, 10 parts bismuth subnitrate, 10 parts pulverized starch, and 50 parts of 1% dibucaine or 20% benzocaine in an ointment base, the ratio of phenol to menthol being about 2 to 1, said menthol being sufficient in amount to neutralize the unwanted astringent properties of the phenol and less than the amount to cause crystallization of the menthol, said preparation includes and are in the proportions by weight of 0.6 gr phenol, 0.3 gr menthol, 10 gr bismuth subnitrate, 10 gr pulverized starch, and 50 gr of 1% by weight dubucaine in an ointment base of lanolin and petrolatum.

* * * * *